(12) United States Patent  (10) Patent No.: US 8,983,031 B2
Rau et al.  (45) Date of Patent: Mar. 17, 2015

(54) IRRADIATION PLANNING AND IRRADIATION FOR A QUASI-CYCLICALLY MOVING TARGET VOLUME

(75) Inventors: Andreas Rau, Erlangen (DE); Martin Tacke, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 281 days.

(21) Appl. No.: 13/565,611

(22) Filed: Aug. 2, 2012

(65) Prior Publication Data

US 2013/0195247 A1 Aug. 1, 2013

(30) Foreign Application Priority Data

Aug. 3, 2011 (DE) .......................... 10 2011 080 368

(51) Int. Cl.
*A61N 5/10* (2006.01)
(52) U.S. Cl.
CPC ................................... *A61N 5/1037* (2013.01)
USPC .......................................................... 378/65
(58) Field of Classification Search
CPC ..... A61N 5/1042; A61N 5/1037; H05G 1/46; H05G 1/38; A61B 6/542
USPC .......................................................... 378/65
See application file for complete search history.

(56) References Cited

U.S. PATENT DOCUMENTS 7,769,430 B2 8/2010 Mostafavi
2012/0061582 A1 3/2012 Iwata

FOREIGN PATENT DOCUMENTS

EP 2 436 424 A1 4/2012

OTHER PUBLICATIONS

G. Zhang et al. "Motion weighted target volume and dose volume histogram: A practical approximation of four dimensional plannign and evaluation," Radiotherapy and Oncology 99, pp. 67-72 (2011).*
German Office Action dated Jun. 28, 2012 for corresponding German Patent Application No. DE 10 2011 080 368.8 with English translation.
G. Zhang et al., "Motion-weighted target volume and dose-volume histogram: A practical approximation of four-dimensional planning and evaluation," Radiotherapy and Oncology 99, pp. 67-72, 2011.
E. Chin et al., "Investigation of a novel algorithm for true 4D-VMAT planning with comparison to tracked, gated and static delivery," Med. Phys. 38, pp. 2698-2707, 2011.

* cited by examiner

*Primary Examiner* — Courtney Thomas
(74) *Attorney, Agent, or Firm* — Lempia Summerfield Katz LLC (57) ABSTRACT

A method for irradiation planning for a quasi-cyclically moving target volume includes defining a first movement phase within a movement period of the target volume and carrying out a first irradiation planning using a first position of the target volume during the first movement phase. The method also includes defining a second movement phase within the movement period of the target volume, and carrying out a second irradiation planning for the second movement phase using a second position of the target volume during the second movement phase. An apportionment of a total dose to be applied is provided to a first partial dose that is allocated to the first movement phase and to a second partial dose that is allocated to the second movement phase.

20 Claims, 4 Drawing Sheets

IRRADIATION PLANNING AND IRRADIATION FOR A QUASI-CYCLICALLY MOVING TARGET VOLUME

This application claims the benefit of DE 10 2011 080 368.8, filed on Aug. 3, 2011.

BACKGROUND

The present embodiments relate to a method and a device for irradiation planning or for irradiation for a quasi-cyclically moving target volume.

Radiation therapy is an established method for the treatment of tumorous diseases. Radiation therapy involves directing high-energy treatment radiation (e.g., high-energy X-ray radiation) at tissue that is to be irradiated (e.g., a tumor).

Radiation therapy of moving target volumes (e.g., a pulmonary tumor) presents a challenge, since the part of the body that is to be irradiated moves. The therapeutic radiation is thus applied in a manner that is as well-targeted as possible within the tumor. Also, surrounding tissue is to be shielded from radiation as well as possible. The movement may reduce the accuracy of the irradiation. One option for confronting this uncertainty is to use a greater safety margin, which may, however, lead to healthy tissue being exposed to a greater dose of radiation.

One method that is used in the irradiation of moving tumors is the "gating irradiation method." The gating irradiation method monitors the movement cycle of the target volume, and irradiation occurs when the target volume is located in a specific phase of the movement cycle that is suitable for irradiation.

SUMMARY AND DESCRIPTION

The present embodiments may obviate one or more of the drawbacks or limitations in the related art. For example, an apparatus and a method for irradiation planning or for irradiation for a quasi-cyclically moving target volume that allows quick and precisely directed irradiation of the target volume while shielding surrounding tissue from radiation is provided.

The method for irradiation planning for a quasi-cyclically moving target volume includes defining a first movement phase within a movement period of the target volume, carrying out a first irradiation planning, using a first position of the target volume during the first movement phase, and defining a second movement phase within the movement period of the target volume. The method also includes carrying out a second irradiation planning for the second movement phase, and using a second position of the target volume during the second movement phase. The total dose is apportioned to a first partial dose that is allocated to the first movement phase and to a second partial dose that is allocated to the second movement phase.

For irradiation of a quasi-cyclically moving target volume, the irradiation planning is to be appropriately designed.

A quasi-cyclically moving target volume is, for example, a lung or the liver. The quasi-cyclical moving target has a quasi-cyclic movement as a result of, for example, inhalation and exhalation, the beating heart, and the intestine and the organs surrounding the intestine, as the contractions of the intestine have a certain regularity.

Conventional gating methods, in which the radiation is applied only during a single gating time window within the movement period, have an unfavorable effect on the total duration of irradiation, since the part of the movement period that is outside the gating time window remains unused for the actual irradiation.

In the present embodiments, two gating time windows (e.g., a plurality of different gating time windows) may be used within a movement period in order to irradiate the target volume. For example, a tumor of the lung or liver may be irradiated both during the inhalation phase and during the exhalation phase.

Such an irradiation is incorporated in the irradiation planning. This is achieved by two different movement phases or gating time windows (e.g., a plurality of different movement phases or gating time windows), during which radiation may be applied, defined within one movement period during the irradiation planning. In these various movement phases, different anatomical circumstances are observed. These different anatomical circumstances (e.g., the different positions of the target volume) also feed into the irradiation planning.

A first partial irradiation plan is established for the irradiation of the target volume in the first movement phase based on the anatomical circumstances that are prevalent in the first movement phase.

The anatomical circumstances may be defined using a four-dimensional data set, for example, such as a 4D-CT. A second partial irradiation plan is established for the irradiation of the target volume in the second movement phase based on how the anatomical circumstances have changed in comparison with the first movement phase. In addition to the two irradiation phases, the second partial irradiation plan may optionally incorporate further irradiation phases, for which the same procedure applies, depending on the movement that is observed. The total dose to be applied is apportioned to the two different movement periods, such that the sum of the individually allocated partial doses provides the total dose that is to be applied. The irradiation planning for the individual movement phases may be carried out using the total dose apportioned in advance to the two partial doses.

The first movement phase may, for example, include a greater proportion of the total duration of a movement cycle than the second movement phase does. The apportionment may be arranged such that the first partial dose is greater than the second partial dose. For example, the apportionment of the total dose may be provided such that the apportionment is proportional to the portion that the duration of the respective movement phases represents in the total duration of the movement cycle.

For example, two movement phases that are allocated to the exhalation position and the inhalation position may be used. The duration of the exhalation position may, for example, amount to an average of 40% of the movement cycle and the duration of the inhalation position to 20% of the movement cycle. Accordingly, two thirds of the total dose that is to be applied is allocated to the exhalation phase, and one third of the total dose that is to be applied is allocated to the inhalation phase.

In the first irradiation planning, a plurality of segments may be defined. The first partial dose is applied with the aid of the plurality of segments defined in the first irradiation planning. The segments may indicate how the radiation is to be limited laterally in order to achieve the desired dose distribution in the target volume for the first partial irradiation plan (e.g., in order to meet objectives regarding the dose to be applied in the target volume and with respect to the maximum dose that is to be tolerated in the tissue that is to be shielded from radiation). The segments in the first irradiation planning are adapted or optimized for the anatomical circumstances in the object to be irradiated during the first movement phase.

In the second irradiation planning, a plurality of segments may be defined. The second partial dose may be applied with the aid of the plurality of segments defined in the second irradiation planning. The segments may indicate how the radiation should be limited laterally in order to achieve the desired dose allocation in the target volume for the second partial irradiation plan. The segments in the second irradiation planning are adapted or optimized to the anatomical circumstances in the object to be irradiated during the second movement phase.

At the end of the irradiation planning, an irradiation plan including two partial irradiation plans (e.g., a plurality of partial irradiation plans) may be established. The first partial irradiation plan includes the parameters optimized for the irradiation of the target volume with the first partial dose in the first movement phase; the second partial irradiation plan includes the parameters optimized for the irradiation of the target volume with the second partial dose in the second movement phase.

An irradiation plan or the two partial irradiation plans may be implemented by a radiation therapy device or a control unit of the radiation therapy device such that the radiation therapy device is controlled to apply the dose according to the irradiation planning.

In one embodiment, an apparatus for irradiation planning for a quasi-cyclically moving target volume includes a processor unit (e.g., a processor). The processor is configured to define a first movement phase within a movement period of the target volume, and carry out a first irradiation planning using a first position of the target volume during the first movement phase. The processor is also configured to define a second movement phase within the movement period of the target volume, and carry out a second irradiation planning for the second movement phase using a second position of the target volume during the second movement phase. A total dose to be applied is apportioned to a first partial dose that is allocated to the first movement phase and to a second partial dose that is allocated to the second movement phase.

The apparatus may be configured to carry out one of the above methods for irradiation planning, for example, by appropriate configuration or programming of the processor unit.

In another embodiment, a method for irradiation for a quasi-cyclically moving target volume includes monitoring movement of the target volume and detecting that the target volume has entered a first movement phase. The first movement phase is a first section of a movement cycle of the target volume. The method also includes applying part of a first partial dose of the total dose. The first partial dose is allocated to the first movement phase when the target volume is in the first movement phase. The method includes detecting that the target volume has entered a second movement phase. The second movement phase is a second section of the movement cycle of the target volume. The method also includes applying part of a second partial dose of the total dose. The second partial dose is allocated to the second movement phase when the target volume is in the second movement phase. Detecting that the target volume has entered a first movement phase, applying part of the first partial dose, detecting that the target volume has entered the second movement phase, and applying part of the second partial dose are repeated (e.g., repeated acts) a plurality of times until the entire first predefined partial dose of the total dose has been applied when the target volume is in the first movement phase or until the entire second predefined partial dose of the total dose is applied when the target volume is in the second movement phase.

This may eventually lead to the repeated acts being repeated a plurality of times until the entire first predefined partial dose of the total dose has been applied when the target volume is in the first movement phase and until the entire second predefined partial dose of the total dose has been applied when the target volume is in the second movement phase. The repeated acts may be skipped for a movement phase if the entire planned partial dose for this movement phase has already been applied.

In this irradiation method, irradiation takes place within one movement cycle at two different points of time or sections (e.g., a plurality of different points of time or sections).

When the target volume enters the first movement phase of the movement period, a first gating time window opens. During the first gating time window, the application of radiation occurs, and part of the first partial dose is applied. The first partial dose has been defined beforehand during the irradiation planning and allocated to the first movement phase. The first partial irradiation plan is established for the first partial dose. This application of radiation takes place according to the parameter settings defined for the first partial irradiation plan. As soon as the target volume leaves the first movement phase in the movement period, the first gating time window ends, and the application of radiation is interrupted.

In the same movement cycle, when the target volume enters the second movement phase of the movement period, a second gating time window opens. During the second gating time window, radiation is again applied. Part of the second partial dose is applied. The second partial dose is allocated to the second partial irradiation plan and is defined beforehand during the irradiation planning for the second movement phase. This application of the radiation takes place according to the settings defined for the second partial irradiation plan. As soon as the target volume leaves the second movement phase, the application of radiation is interrupted again.

The target volume may optionally be irradiated during further predefined gating time windows in the same movement cycle.

In the movement cycle that follows, there is again a waiting period until the target volume enters the first movement phase. In the present gating time window, which is allocated to the first movement phase, radiation is again applied. Once again, part of the first partial dose is applied. The first partial dose is allocated to the first partial irradiation plan. If, in the same movement cycle, the target volume again enters the second movement phase, a new gating time window allocated to the second movement phase opens. Again, part of the second partial dose is emitted. The second partial dose is allocated to the second partial irradiation plan.

This method may be further continued. In consecutive movement cycles, the target volume is thus irradiated twice (e.g., a plurality of times) per movement cycle with alternating parameter settings. Each of the parameter settings is defined specifically beforehand for the different movement phases and set down in partial irradiation plans.

The repeated acts are repeated alternately in consecutive movement cycles. This may be carried out until the entire first partial dose or the entire second partial dose has been applied as planned. The remainder of the particular partial dose that has not yet been applied entirely is applied, the irradiation taking place in the relevant irradiation phase.

The part of the movement period that is available for irradiation and is significantly limited by conventional gating methods is used more effectively, since a plurality of gating windows are available during one movement period.

Relatively slight deviations in the dose may be averaged out more effectively. A slight error may occur with each gating window. As a result of the dose being applied in a plurality of movement phases and hence in different gating time windows, slight deviations in dose may be averaged out more effectively.

For example, if, in the irradiation planning, the total dose has been apportioned into the individual partial doses according to the durations of the individual movement phases as a function of the total duration of the movement cycle, the total dose may be applied quickly, since the period of time available for irradiation during the movement cycles may be utilized in a favorable manner as a result of this variant. The remainder of that partial dose that remains to be applied when the other partial dose has already been emitted entirely is small.

The movement cycle is utilized more effectively in such an irradiation method than in irradiation methods in which only one gating time window is used for irradiation during a movement cycle. Since a gating method is used, irradiation may be avoided during certain movement phases, during which, for example, the target volume is moving too fast for precisely targeted irradiation of the target volume to be possible.

The first movement phase and the second movement phase may occur such that the target volume is in a third movement phase between a gating window in the first movement phase and the subsequent gating window in the second movement phase. During the third movement phase, radiation is not applied, but a changeover of the machine parameters from a first setting, established for the application of the first partial dose, to a second setting, established for the subsequent application of the second partial dose, occurs.

With this embodiment, the movement phase in which no application of radiation takes place is advantageously utilized to change the machine parameters on the radiation therapy device from the application of the first partial dose to the application of the second partial dose, for example, with respect to shapes of the segments that are to be applied.

In one embodiment of the method, the application of the first partial dose and/or the second partial dose during the first movement phase or the second movement phase, respectively, may be done in segments. For example, a segment may be characterized by a particular collimator aperture, with which the duration of the treatment radiation is limited.

The method may be configured such that only one segment is applied in each case during a gating window in the first movement phase. Such a configuration may be incorporated more easily into a radiation therapy device or the control apparatus of the radiation therapy device, since a fast changeover from one segment to the next during the same gating time window makes high demands on the speed with which the parameter settings are changed.

In another embodiment of the method, during a gating window in the first movement phase, the application of a segment dose allocated to a segment is discontinued, and the application of a subsequent segment dose allocated to a subsequent segment is initiated in the same gating time window. This embodiment allows even faster application of the total radiation dose but uses a more complex control of the radiation therapy device or makes more demands on the speed with which the parameter settings are changed. A plurality of different segments may be applied within one gating window.

In one embodiment of the method, the application of a segment dose allocated to one segment may be initiated during a gating window and continued during the subsequent gating window in the same movement phase. This allows applying incomplete segment doses in a gating time window. In the event of incomplete application, the irradiation is continued in the next gating time window, using the parameter setting allocated to this segment, until the planned accumulated dose is reached.

In one embodiment, an irradiation apparatus includes an X-ray source to provide therapeutic radiation, with which a target volume may be irradiated. The irradiation apparatus also includes a movement monitoring device configured to detect the movement of a target volume. The irradiation apparatus includes a control apparatus configured to control the application of radiation using the movement of the target volume detected by the movement monitoring device. The control apparatus is configured to carry out, when in operation, an irradiation method, as described above.

The control apparatus may define whether a machine adjustment allocated to the first movement phase is to be carried out if there is a gating time window allocated to the first movement phase, or whether a machine adjustment allocated to the second movement phase is provided if a corresponding gating window is present.

The description in the aforementioned and hereafter of the individual features, the advantages thereof, and the effects thereof relates both to the apparatus category and to the method category although this is not mentioned explicitly in detail in every case. The individual features disclosed may also be fundamental to the invention in combinations other than those shown. The description of advantages and effects that have been disclosed in connection with irradiation planning also applies to irradiation, and vice versa.

DETAILED DESCRIPTION OF THE DRAWINGS

Figure 1:
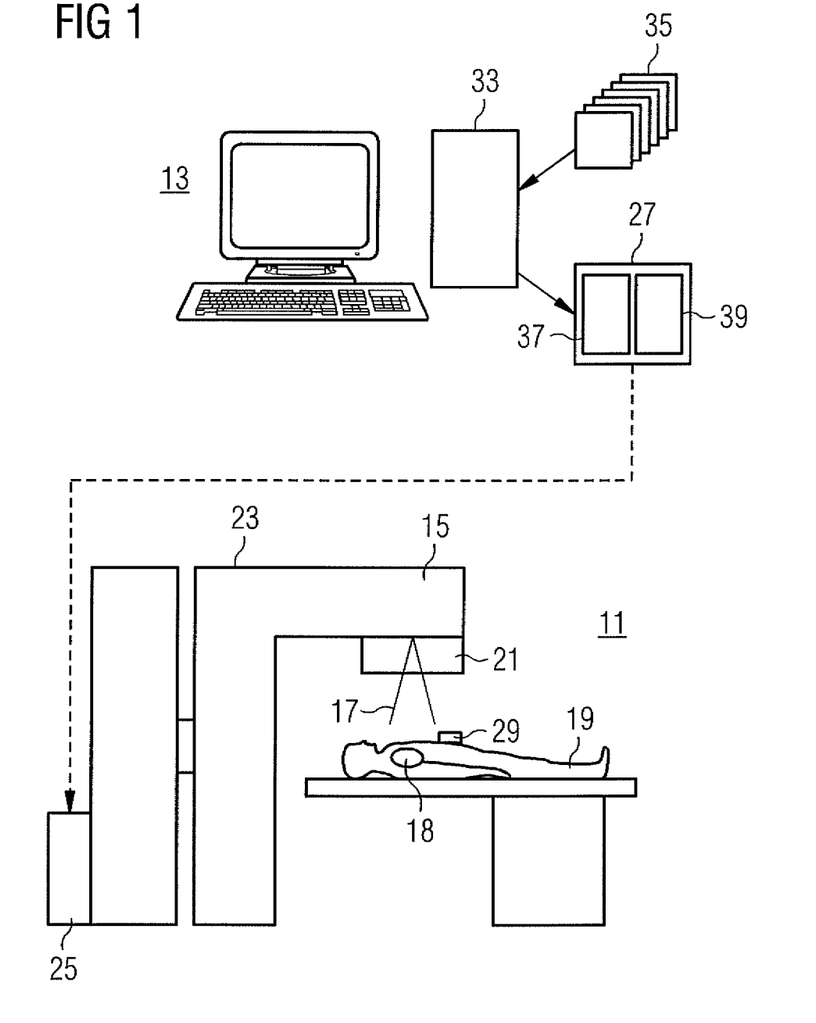
FIG. 1 shows a schematic overview of one embodiment of a radiation therapy device and of an irradiation planning device.

FIG. 1 provides a rough schematic outline of the design of a radiation therapy device 11 and an irradiation planning apparatus 13.

The radiation therapy device 11 has a therapeutic X-ray source 15, with which treatment radiation 17 may be directed onto a patient 19. The treatment radiation 17 may be used to irradiate a quasi-cyclically moving lung 18, for example. The radiation therapy device 11 further includes an apparatus, with which the treatment radiation 17 may be modified such that the treatment radiation 17 may be emitted according to an irradiation plan. The apparatus includes, for example, a collimator 21, with which "segments" of an irradiation planning data set may be set and emitted.

A segment is characterized by a certain dose and by a certain collimator aperture that limits a lateral extent of the treatment radiation 17 and with which the dose is emitted.

The radiation therapy device 11 may include a rotatable gantry 23, with which the individual segments may be directed at the patient 19 from different directions.

A control device 25 (e.g., a control apparatus, a controller, or a processor) for the radiation therapy device 11 controls the components of the radiation therapy device 11 such that an irradiation plan 27 that is provided via an interface in the control apparatus 25 may be applied using the radiation therapy device 11.

The control apparatus 25 also includes an interface, through which data describing the movement of the target volume in the patient 19 may be input. Such movement data may be recorded via external sensors 29, for example.

The irradiation planning apparatus 13 may be installed in a processor unit 33 that has been programmed and configured for irradiation planning.

The processor unit 33 has a port for loading the patient data set 35 (e.g., a four-dimensional computed tomography data set (4D-CT)).

On the basis of this, the user may establish irradiation planning by inputting certain required objectives, according to which irradiation is to be carried out. The irradiation plan 27 is subsequently established, ultimately determining the parameter settings, with which the requirements of a desired irradiation may be met with optimum efficiency, and recording the parameter settings in a data set (e.g., the irradiation plan 27).

The control apparatus 25 for the radiation therapy device and the irradiation planning apparatus 31 may be configured such that the control apparatus 25 and the irradiation planning apparatus may be used to carry out the methods of the present embodiments.

The irradiation plan 27 includes two partial irradiation plans 37, 39 (e.g., a plurality of partial irradiation plans).

Figure 2:
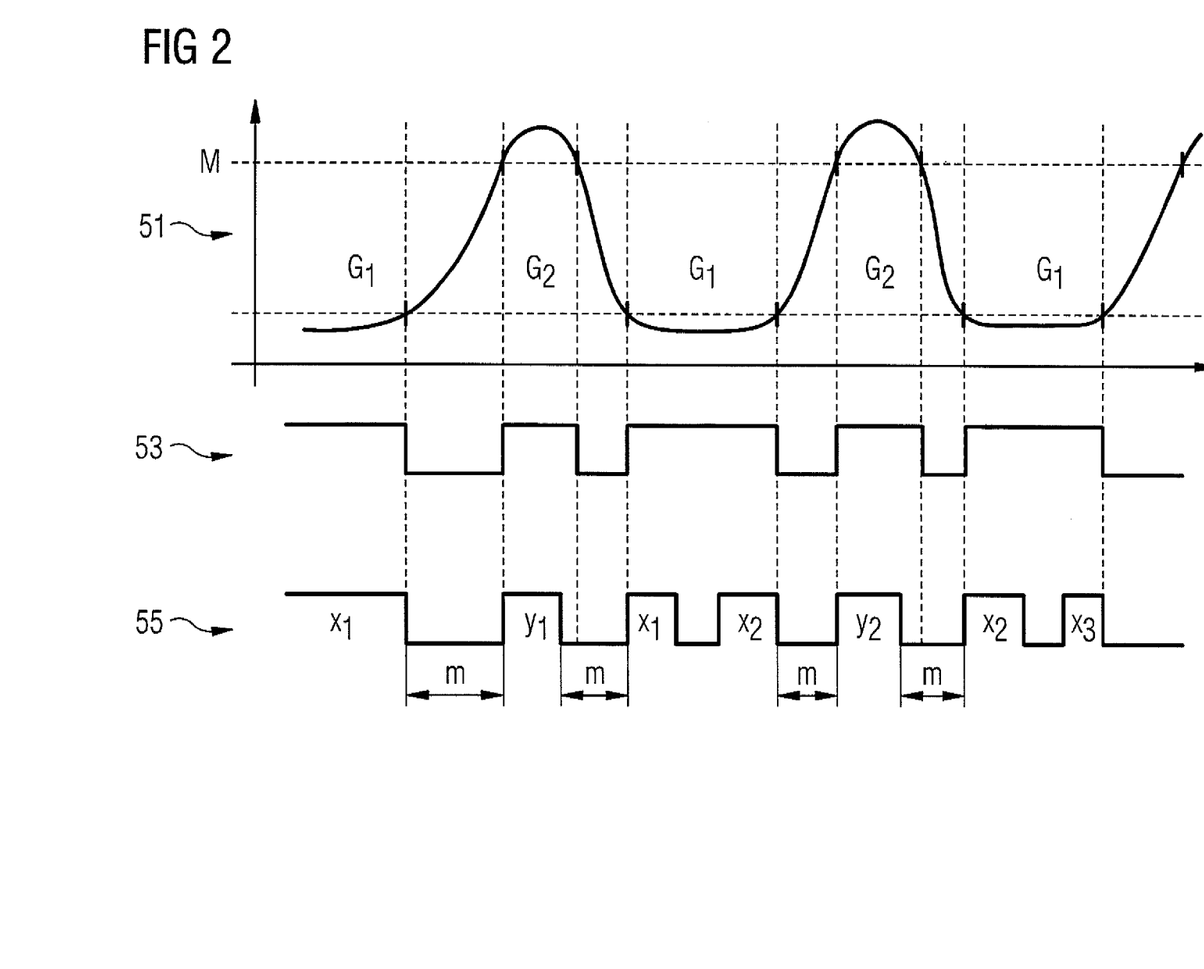
FIG. 2 shows a diagram illustrating an exemplary chronological sequence of movement over a plurality of movement cycles.

The top curve 51 in FIG. 2 shows a chronological sequence of a breathing movement M of the lung, using a one-dimensional signal. Such a signal may be provided, for example, by an external sensor (e.g., a breath sensor).

The top curve 51 shows a plurality of consecutive movement cycles. FIG. 2 further shows the movement phases in the movement cycles that correspond to an inhalation position $G_2$ or an exhalation position $G_1$. The movement phases, in which radiation may be applied, may occur in the inhalation position $G_2$ and the exhalation position $G_1$. In movement phases that are located between the inhalation position and the exhalation position, the radiation is not applied.

This situation is shown in the second curve 53, which appears below the breathing curve and shows gating time windows (e.g., time segments, in which the treatment radiation may be switched on to apply the dose).

In each movement cycle, there are two gating time windows (e.g., a gating time window for inhalation $G_2$, and a gating time window for exhalation $G_1$).

The third curve 55 shows the time segments, in which irradiation actually takes place ("Beam ON").

The time segments are labeled with $x_i$ or $y_i$. The reference sign $x_i$ denotes the segments that are allocated to a first partial irradiation plan (e.g., exhalation phase), and $y_i$ denotes the segments that are allocated to a second partial irradiation plan (e.g., inhalation phase).

A possible configuration for irradiation is shown using irradiation during the exhalation phase ($G_1$).

In this irradiation, the first partial irradiation plan is emitted (e.g., the segments $x_i$; the dose allocated to the segment $x_1$ is applied during the first gating time window of the exhalation phase). At the end of this gating time window, the dose for the segment $x_1$ has not yet been applied entirely, however. The irradiation of the segment $x_1$ is therefore continued in the subsequent gating time window of the exhalation phase. During this gating time window, the irradiation of the $x_1$ segment dose is terminated before the end of the gating time window has been reached.

The time remaining in the gating time window is used to adjust the radiation therapy device for the irradiation of the next segment $x_2$ and to apply the dose allocated to this segment. The gating time window ends before the entire dose for the segment $x_2$ has been applied. The irradiation is therefore continued in the next gating time window in the exhalation phase.

One embodiment of irradiation is shown using irradiation during the inhalation phase ($G_2$). In this movement phase, the second partial irradiation plan (e.g., segments $y_i$) is emitted.

The irradiation is carried out such that only one segment $y_i$ or the dose associated with the one segment $y_i$ may be emitted during one gating time window. As soon as the emission of this dose has come to an end, the time remaining in the one gating time window is not used for a further irradiation. The dose for the next segment is only started in the subsequent gating time window and (if possible) emitted until complete.

In this variant, a segment is consequently applied during one gating window or during a plurality of gating windows (e.g., if a plurality of gating windows are required). However, no different segments are selected and applied during one gating window.

The intervals labeled with in indicate the phases in which radiation is not applied, and in which the machine parameters are changed from the irradiation of the first partial irradiation plan to irradiation of the second partial irradiation plan, and vice versa.

Figure 3:
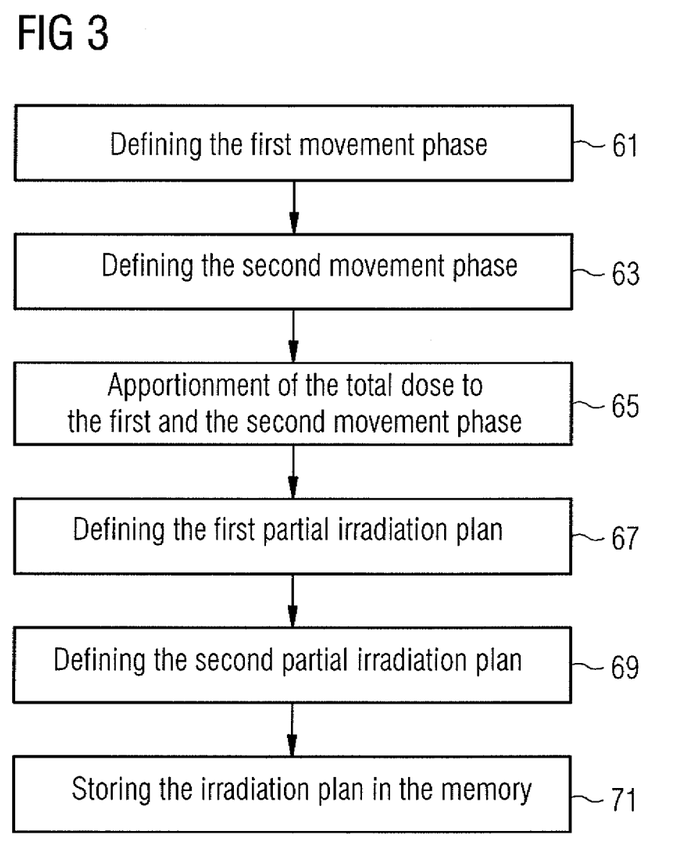
FIG. 3 shows a flow chart of one embodiment of a method for carrying out irradiation planning.

FIG. 3 shows a schematic flow diagram for one embodiment of carrying out irradiation planning.

In act 61, a first movement phase, for which a first partial irradiation plan may be established, is defined within a first movement period of the target volume.

In act 63, a second movement phase is defined within a second movement period of the target volume. The second movement period is different and separate from the first movement phase. A second partial irradiation plan may be established for the second movement phase.

The first movement phase and the second movement phase (e.g., a plurality of movement phases) may be defined and selected using a four-dimensional CT-data set.

The duration of the first movement phase and the duration of the second movement phase are compared with each other. A total dose to be applied is apportioned, according to a relationship between the duration of the first movement phase and the duration of the second movement phase, to a first partial dose that is to be applied only during the first movement phase, and to a second partial dose that is to be applied only during the second movement phase (act 65). The weighting of the segments is therefore based on the length of the estimated period that the target volume remains in the respective movement phases (e.g., the first movement phase and the second movement phase).

A first partial irradiation plan is established based on the anatomical circumstances in the first movement phase. In the first partial irradiation plan, the first partial dose of the total dose may be applied. In order to establish the first partial irradiation plan, known methods may be used for irradiation planning (act 67).

A second partial irradiation plan is established for the second movement phase. The second partial irradiation plan is based on the anatomical circumstances in the second movement phase. The second partial dose of the total dose may be applied with the second partial irradiation plan. In order to establish the second partial irradiation plan, known methods may be used for irradiation planning (act 69).

The irradiation plan (e.g., including both the first partial irradiation plan and the second partial irradiation plan) is stored (act 71).

Figure 4:
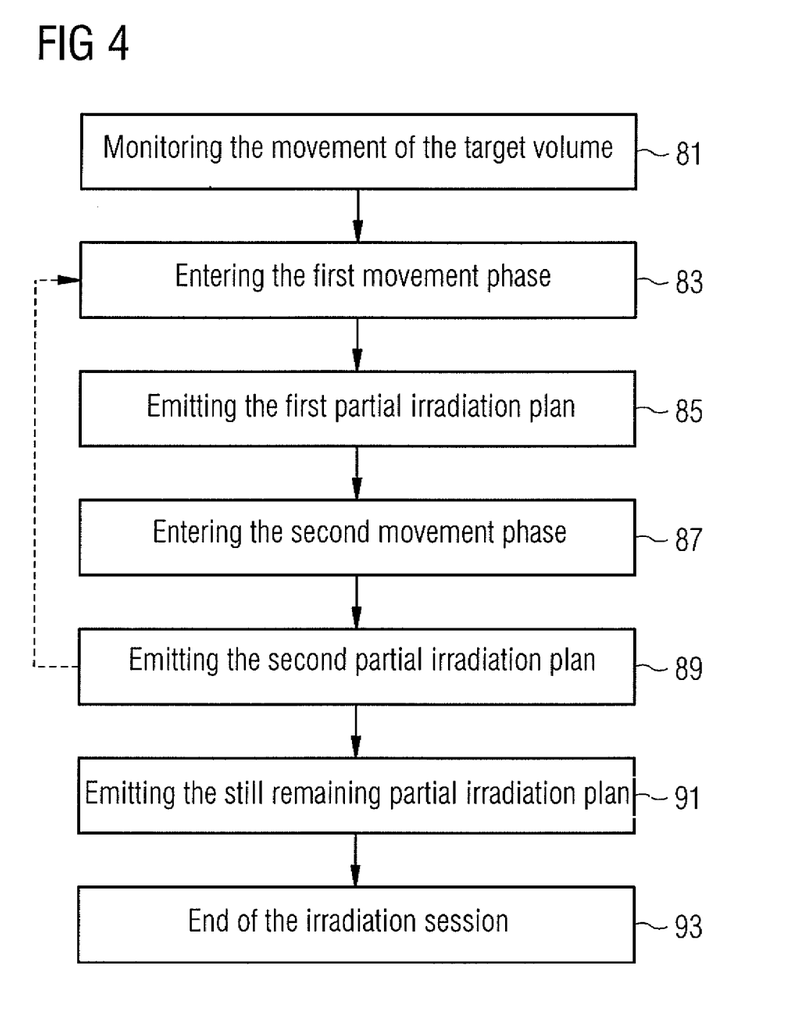
FIG. 4 shows a flow chart of one embodiment for carrying out irradiation.

FIG. 4 shows a schematic flow diagram demonstrating how an irradiation plan that has been established using a method according to, for example, FIG. 3 may be emitted.

During the irradiation of the target volume, the movement of the target volume is monitored continuously. For example, a movement signal is recorded and analyzed (act 81).

This movement signal is used to derive a gating signal (e.g., a signal that informs the radiation therapy device when a gating window begins ("Gate-On") and when a gating windows ends ("Gate-Off")). This may be carried out, for example, by a separate system that is arranged in series between the movement monitor and the radiation therapy system. This may also be carried out by a control apparatus in the radiation therapy system.

The apparatus, with which the gating signal is derived from the movement signal, may also provide further information indicating the movement phase to which the gating signal is allocated. This may be achieved in various ways. For example, the gating signal for the various movement phases may be provided to the irradiation system via one or a plurality of cables. If the gating signal is transmitted via a cable, the gating signal may be encoded in order to allocate the gating signal to the movement phase. The encoding may, for example, be a complete signal in a TCP/IP-protocol with allocation to the movement phases. In an analog signal, the encoding may be achieved, for example, by various voltage levels or encoding in different frequencies.

In one embodiment, the gating signal may be transmitted to the irradiation system in an unencoded form. In such a case, the irradiation system establishes the allocation to the movement phases.

The target volume is observed entering the first movement phase (act 83). When the target volume is in this first movement phase, the application of the first partial irradiation plan begins (act 85). As soon as the target volume comes out of the first movement phase, the irradiation of the first partial irradiation plan stops.

It is subsequently established that the target volume is entering the second movement phase (act 87). In the meantime, the radiation therapy device is reset to emit the second partial irradiation plan. When the target volume is in this second movement phase, the application of the second partial irradiation plan begins (act 89). As soon as the target volume comes out of the second movement phase, the irradiation of the second partial irradiation plan stops.

Acts 83 to 89 are repeated until the first partial irradiation plan or the second partial irradiation plan have been applied entirely.

The still remaining partial irradiation plan, which has not yet been applied entirely, is irradiated (act 91).

After the first partial irradiation plan and the second partial irradiation plan have been emitted entirely, the irradiation session ends (act 93).

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for irradiation planning for a target volume that is moving quasi-cyclically, the method comprising:
defining a first movement phase within a movement period of the target volume;
carrying out a first irradiation planning using a first position of the target volume during the first movement phase;
defining a second movement phase within the movement period of the target volume;
carrying out a second irradiation planning using a second position of the target volume during the second movement phase; and,
apportioning a total dose to be applied, the apportioning comprising allocating a first partial dose to the first movement phase and allocating a second partial dose to the second movement phase.

2. The method as claimed in claim 1, wherein the first movement phase comprises a greater portion of a total duration of a movement cycle than the second movement phase, and
wherein apportioning comprises apportioning such that the first partial dose is greater than the second partial dose.

3. The method as claimed in claim 2, wherein apportioning the total dose comprises apportioning the total dose proportionally to the portions that durations of the first movement phase and the second movement phase, respectively, represent in the movement cycle.

4. The method as claimed in claim 1, further comprising defining a plurality of segments during each of the first irradiation planning and the second irradiation planning, the first partial dose and the second partial dose being applied through the plurality of segments.

5. The method as claimed in claim 2, further comprising defining a plurality of segments during each of the first irradiation planning and the second irradiation planning, the first partial dose and the second partial dose being applied through the plurality of segments.

6. The method as claimed in claim 3, further comprising defining a plurality of segments during each of the first irradiation planning and the second irradiation planning, the first partial dose and the second partial dose being applied through the plurality of segments.

7. An apparatus for irradiation planning for a target volume moving quasi-cyclically, the apparatus comprising:
a processor configured to:
detect a first movement phase within a movement period of the target volume;
carry out a first irradiation planning using a first position of the target volume during the first movement phase;
detect a second movement phase within the movement period of the target volume;
carry out a second irradiation planning for the second movement phase using a second position of the target volume during the second movement phase; and
apportion a total dose to be applied, such that a first partial dose is allocated to the first movement phase, and a second partial dose is allocated to the second movement phase.

8. The apparatus as claimed in claim 7, wherein the first movement phase comprises a greater portion of a total duration of a movement cycle than the second movement phase, and
wherein the processor is configured to apportion the total dose such that the first partial dose is greater than the second partial dose.

9. The method as claimed in claim 8, wherein the processor is configured to apportion the total dose such that the total dose is apportioned proportionally to the portions that durations of the first movement phase and the second movement phase, respectively, represent in the movement cycle.

10. The method as claimed in claim 7, wherein the processor is further configured to define a plurality of segments during each of the first irradiation planning and the second irradiation planning, the first partial dose and the second partial dose being applied through the plurality of segments.

11. A method for the irradiation of a target volume moving quasi-cyclically, the method comprising:
monitoring movement of the target volume;
determining when the target volume has entered a first movement phase, the first movement phase being a first section of a movement cycle of the target volume;
applying part of a first partial dose of a total dose, the first partial dose being allocated to the first movement phase when the target volume is in the first movement phase;
determining when the target volume has entered a second movement phase, the second movement phase being a second section of the movement cycle of the target volume; and
applying part of a second partial dose of the total dose, the second partial dose being allocated to the second movement phase when the target volume is in the second movement phase,
wherein determining when the target volume has entered the first movement phase, applying part of the first partial dose, determining when the target volume has entered the second movement phase, and applying part of the second partial dose are repeated until the entire first partial dose of the total dose has been applied when the target volume is in the first movement phase, or until the entire second partial dose of the total dose has been applied when the target volume is in the second movement phase.

12. The method as claimed in claim 11, wherein the target volume is located in a third movement phase between one gating window in the first movement phase and a subsequent gating window in the second movement phase, and
wherein the method further comprises changing, during the third movement phase, machine parameters from a first parameter setting, established for the application of the first partial dose, to a second parameter setting, established for the subsequent application of the second partial dose, radiation not being applied during the third movement phase.

13. The method as claimed in claim 11, wherein applying part of the first partial dose comprises applying part of the first partial dose in segments, and
wherein only one of the segments is applied during one gating window in the first movement phase.

14. The method as claimed in claim 11, wherein applying part of the first partial dose comprises applying part of the first partial dose in segments, and
wherein the method further comprises terminating, during a gating window of the first movement phase, application of a segment dose assigned to one of the segments, and initiating the application of a next segment dose allocated to another of the segments, the other segment being subsequent to the one segment.

15. The method as claimed in claim 11, wherein applying part of the first partial dose comprises applying a first predefined partial dose during the first movement phase in segments, and
wherein the method further comprises initiating, during a gating window, the application of a segment dose allocated to a segment, and continuing, during a subsequent gating window, in the same movement phase.

16. The method as claimed in claim 12, wherein applying part of the first partial dose comprises applying part of the first partial dose in segments, and
wherein only one of the segments is applied during one gating window in the first movement phase.

17. The method as claimed in claim 12, wherein applying part of the first partial dose comprises applying part of the first partial dose in segments, and
wherein the method further comprises terminating, during a gating window of the first movement phase, application of a segment dose assigned to one of the segments, and initiating the application of a next segment dose allocated to another of the segments, the other segment being subsequent to the one segment.

18. The method as claimed in claim 12, wherein applying part of the first partial dose comprises applying a first predefined partial dose during the first movement phase in segments, and
wherein the method further comprises initiating, during a gating window, the application of a segment dose allocated to a segment, and continuing, during a subsequent gating window, in the same movement phase.

19. The method as claimed in claim 13, wherein applying part of the first partial dose comprises applying part of the first partial dose in segments, and
wherein the method further comprises terminating, during a gating window of the first movement phase, application of a segment dose assigned to one of the segments, and initiating the application of a next segment dose allocated to another of the segments, the other segment being subsequent to the one segment.

20. An irradiation apparatus comprising:
an X-ray source operable to provide therapeutic radiation, with which a target volume is irradiated;
a movement monitoring device configured to detect a movement of the target volume; and
a controller configured to control application of radiation using the movement of the target volume detected by the movement monitoring device, the controller further configured to:
determine when the target volume has entered a first movement phase, the first movement phase being a first section of a movement cycle of the target volume;
apply part of a first partial dose of a total dose, the first partial dose being allocated to the first movement phase when the target volume is in the first movement phase;
determine when the target volume has entered a second movement phase, the second movement phase being a second section of the movement cycle of the target volume; and
apply part of a second partial dose of the total dose, the second partial dose being allocated to the second movement phase when the target volume is in the second movement phase,
wherein the controller is configured to determine when the target volume has entered the first movement phase, apply part of the first partial dose, determine when the target volume has entered the second movement phase, and apply part of the second partial dose repeatedly until the entire first partial dose of the total dose has been applied when the target volume is in the first movement phase, or until the entire second partial dose of the total dose has been applied when the target volume is in the second movement phase.

* * * * *